United States Patent [19]

Figlia et al.

[11] Patent Number: 4,658,444

[45] Date of Patent: Apr. 21, 1987

[54] SURGICAL GLOVES

[76] Inventors: Betty J. Figlia, 520 E. 72nd St., Apt. 10-0, New York, N.Y. 10021; George Spector, 233 Broadway, Rm 3815, New York, N.Y. 10007

[21] Appl. No.: 900,001

[22] Filed: Aug. 25, 1986

[51] Int. Cl.4 .................................................. A41D 19/00
[52] U.S. Cl. ............................................. 2/161 R; 2/168
[58] Field of Search .............. 2/158, 159, 160, 161 R, 2/161 A, 163, 167, 168, 16, 20, 169, 164; 15/227

[56] References Cited

U.S. PATENT DOCUMENTS

| 792,662 | 6/1905 | Liebenstein | 2/158 |
|---|---|---|---|
| 1,231,168 | 6/1917 | Jones | 2/158 X |
| 1,286,771 | 12/1918 | Raymond | 2/158 |
| 1,643,722 | 9/1927 | Millen | 15/227 |
| 1,786,227 | 12/1930 | Bruggeman | 2/158 X |
| 2,179,614 | 11/1939 | Cohen | 15/227 |
| 2,603,790 | 7/1952 | Boehm-myro | 2/160 X |
| 2,709,824 | 6/1955 | Hall | 15/227 X |
| 3,197,786 | 8/1965 | Velonis et al. | 2/167 |
| 3,608,093 | 9/1971 | Kirby | 2/163 |
| 4,355,424 | 10/1982 | McCoy, Jr. | 2/161 R |
| 4,521,365 | 6/1985 | Kurtz | 264/306 |

FOREIGN PATENT DOCUMENTS

| 988646 | 5/1951 | France | 2/159 |
|---|---|---|---|
| 92959 | 2/1922 | Switzerland | 2/158 |
| 219910 | 9/1942 | Switzerland | 2/158 |
| 787230 | 12/1957 | United Kingdom | 2/159 |

Primary Examiner—Werner H. Schroeder
Assistant Examiner—T. Graveline

[57] ABSTRACT

An improved surgical glove is provided that contains a smooth latex skin coated onto the front surface of the glove so that surgical tape will not stick thereto. A textured contoured flap is pivotly secured to tips of the finger portions of the glove while another textured contoured flap is pivotly secured to tip of the thumb portion of the glove so that when the flaps are flipped over to cover completely the latex skin, the hand of a person wearing the glove can increase its grip to hold various items.

5 Claims, 5 Drawing Figures

SURGICAL GLOVES

BACKGROUND OF THE INVENTION

The instant invention relates generally to gloves and more specifically it relates to an improved surgical glove.

Numerous gloves have been provided in prior art that are adapted to be fabricated out of latex rubber material. For example, U.S. Pat. Nos. 4,218,778; 4,329,312 and 4,371,987 all are illustrative of such prior art. While these units may be suitable for the particular purpose to which they address, they would not be as suitable for the purposes of the present invention as heretofore described.

SUMMARY OF THE INVENTION

A primary object of the present invention is to provide an improved surgical glove that will overcome the shortcomings of the prior art devices.

Another object is to provide an improved surgical glove that is latex coated, which will prevent surgical tape to stick thereto.

An additional object is to provide an improved surgical glove that contains textured contoured flaps which when flipped over will cover the latex coating so that a person wearing the glove can increase their grip.

A further object is to provide an improved surgical glove that is simple and easy to use.

A still further object is to provide an improved surgical glove that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
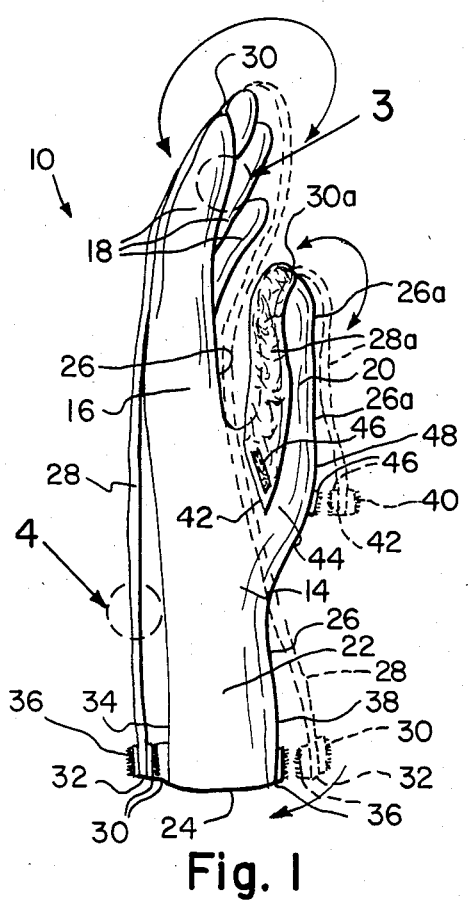
FIG. 1 is a side elevational view of a surgical glove incorporating the invention having a front smooth latex skin and textured contoured flaps that can flip over the surgical glove and be secured by Velcro.
Figure 2:
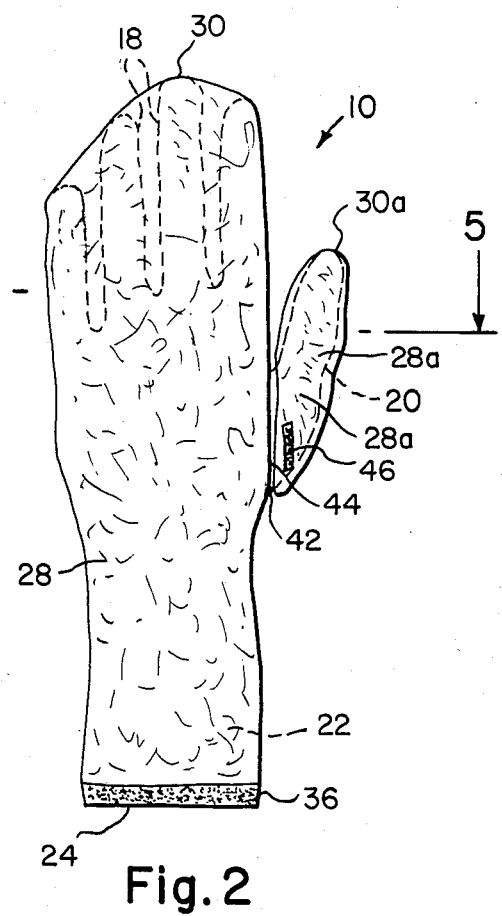
FIG. 2 is a rear elevational view thereof.
Figure 3:
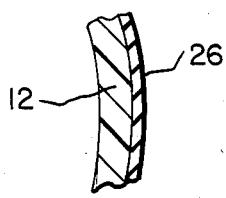
FIG. 3 is an enlarged cross sectional view showing the latex skin in greater detail as indicated by numeral 3 in FIG. 1.
Figure 4:
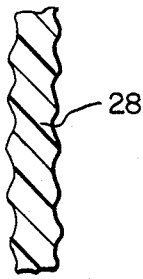
FIG. 4 is an enlarged cross sectional view showing the textured material as indicated by numeral 4 in FIG. 1.
Figure 5:
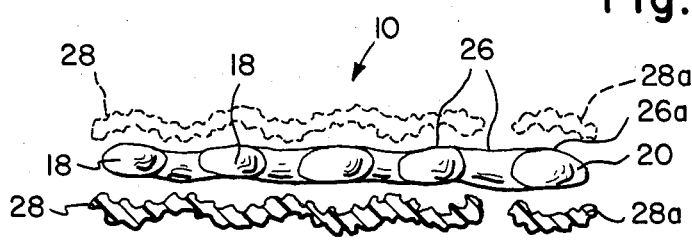
FIG. 5 is a cross sectional view taken along line 5—5 in FIG. 2 showing the textured contoured flaps in greater detail with respect to the fingers and thumb.

Turning now descriptively to the drawings, in which similar reference characters denote similar elements throughout the several views, FIGS. 1 through 5 illustrates an improved surgical glove 10 being formed out of plastic material 12. The glove 10 has a hand portion 14 with a palm area 16, a series of finger portions 18, a thumb portion 20 and a wrist portion 22 that has an opening 24 in which a hand of a person (not shown) is inserted into the glove 10.

The improvement consists of a smooth latex skin 26 coated onto the palm area 16 of the hand portion 14, front of the finger portions 18 and front of the wrist portion 22 so that surgical tape (not shown) will not stick thereto. A textured contoured flap 28 formed out of plastic material is provided and is pivotly secured at 30 to tips of the finger portions 18. When the flap 28 is flipped over, shown in dotted in FIGS. 1 and 5, to cover completely the latex skin 26, the hand of the person wearing the glove 10 can increase its grip to hold various items.

The glove 10 further contains a first fastener 30 for removably securing free end 32 of the flap 28 to rear 34 of the wrist portion 22 when exposing the latex skin 26. A second fastener 36 is for removably securing the free end 32 of the flap 28 to the front 38 of the wrist portion 22 when covering the latex skin 26.

A second smooth latex skin 26a is coated onto front of the thumb portion 20 so that the surgical tape will not stick thereto. A second textured contoured flap 28a formed out of plastic material is pivotly secured at 30a to tip of the thumb portion 20. When the second flap 28a is flipped over, shown in dotted in FIGS. 1 and 5, to cover completely the second latex skin 26a, thumb of the person wearing the glove can increase its grip to hold various items.

The glove 10 further contains a third fastener 40 for removably securing free end 42 of the second flap 28a to rear 44 of the thumb portion 20 when exposing the second latex skin 26a. A fourth fastener 46 is for removably securing the free end 42 of the second flap 28a to front 48 of the thumb portion 20 when covering the second latex skin 26a.

The first fastener 30, the second fastener 36, the third fastener 40 and the fourth fastener 46 are all fabricated out of Velcro. Other types of fasteners (not shown) can also be used to accomplish the desired results such as tape, snaps, buttons and the like.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An improved surgical glove being formed out of plastic material and of the type having a hand portion with a palm area, a series of finger portions, a thumb portion and a wrist portion having an opening in which a hand of a person is inserted into said glove, wherein the improvement comprises:
    (a) a smooth latex skin coated onto said palm area of said hand portion, front of said finger portions and front of said wrist portion so that surgical tape will not stick thereto; and
    (b) a textured contoured flap being formed out of plastic material, pivotly secured to the tips of said finger portions so that when said flap is flipped over to cover completely said latex skin, said hand of said person wearing said glove can increase its grip to hold various items.

2. An improved surgical glove as recited in claim 1, further comprising:

(a) a first means for removably securing free end of said flap to rear of said wrist portion when exposing said latex skin; and (b) a second means for removably securing said free end of said flap to said front of said wrist portion when covering said latex skin.

3. An improved surgical glove as recited in claim 2, further comprising:

(a) a second smooth latex skin coated onto front of said thumb portion so that said surgical tape will not stick thereto; and (b) a second textured contoured flap being formed out of plastic material, pivotly secured to tip of said thumb portion so that when said second flap is flipped over to cover completely said second latex skin, the thumb of said person wearing said glove can increase its grip to hold various items.

4. An improved surgical glove as recited in claim 3, further comprising:

(a) a third means for removably securing free end of said second flap to rear of said thumb portion when exposing said second latex skin; and (b) a fourth means for removably securing said free end of said second flap to front of said thumb portion when covering said second latex skin.

5. An improved surgical glove as recited in claim 4, wherein said first removably securing means, said second removably securing means, said third removably securing means and said fourth removably securing means are all fabricated out of VELCRO-type fastener.

* * * * *